(12) United States Patent
Lin et al.

(10) Patent No.: US 9,051,266 B2
(45) Date of Patent: Jun. 9, 2015

(54) CARBAZOLE DERIVATIVES AND ORGANIC LIGHT EMITTING DIODES COMPRISING THE SAME

(75) Inventors: Jin-Sheng Lin, Tainan (TW);
Mei-Rurng Tseng, Hsinchu (TW);
Miao-Tsai Chu, Sinjhuang (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 534 days.

(21) Appl. No.: 13/447,680

(22) Filed: Apr. 16, 2012

(65) Prior Publication Data
US 2013/0105767 A1 May 2, 2013

(30) Foreign Application Priority Data
Nov. 1, 2011 (TW) .............................. 100139725 A

(51) Int. Cl.
H01L 51/50 (2006.01)
C07D 209/86 (2006.01)
C07D 401/14 (2006.01)
C07D 405/14 (2006.01)
C07D 409/14 (2006.01)
H01L 51/00 (2006.01)

(52) U.S. Cl.
CPC ............ C07D 209/86 (2013.01); C07D 401/14 (2013.01); C07D 405/14 (2013.01); C07D 409/14 (2013.01); H01L 51/0054 (2013.01); H01L 51/0059 (2013.01); H01L 51/0072 (2013.01); H01L 51/0073 (2013.01); H01L 51/0074 (2013.01); H01L 51/5016 (2013.01); Y02E 10/549 (2013.01)

(58) Field of Classification Search
None
See application file for complete search history.

(56) References Cited

U.S. PATENT DOCUMENTS

| 6,602,395 | B1 | 8/2003 | Zhuang et al. |
| 6,630,254 | B2 | 10/2003 | Leclerc et al. |
| 6,917,159 | B2 | 7/2005 | Tyan et al. |
| 7,060,369 | B2 | 6/2006 | Stossel et al. |
| 2008/0036365 | A1 * | 2/2008 | Miki et al. ............... 313/504 |
| 2011/0198579 | A1 * | 8/2011 | Martin et al. ............ 257/40 |

FOREIGN PATENT DOCUMENTS

| CN | 1790771 A | 6/2006 |
| DE | 10 2008 035 413 A1 | 2/2010 |
| JP | 2005-085599 A | 3/2005 |
| JP | 2005-104971 A | 4/2005 |
| JP | 2005-213188 | * 8/2005 ............ C09K 11/06 |
| JP | 2007-230867 A | 9/2007 |
| JP | 2009-035524 A | 2/2009 |
| JP | 2009-40730 A | 2/2009 |
| JP | 2009-104971 A | 5/2009 |
| TW | I312804 | 8/2009 |
| WO | WO 2005/092857 A1 | 10/2005 |
| WO | WO 2008/156656 A2 | 12/2008 |
| WO | WO 2009/124627 A1 | 10/2009 |

OTHER PUBLICATIONS

China Office Action for Appl. No. 201210413818.7 dated May 27, 2014.
Zhang, F. et al, "New Progess of Researches in Carbazole Compounds," Chinese Journal of Organic Chemistry, 2010, vol. 30, No. 6, pp. 783-796.
Taiwan Office Action for Appl. No. 100139725 dated Sep. 23, 2013.
Ikai et al., "Highly Efficient Phosphorescence From Organic Light-Emitting Devices With an Exciton-Block Layer", Applied Physics Letters, Jul. 9, 2001, vol. 79, No. 2, p. 155-158.
Li et al., "Novel Fluorene/Carbazole Hybrids With Steric Bulk as Host Materials for Blue Organic Electrophosphorescent Devices", Elsevier, Tetrahedron, 2007, vol. 63, p. 10161-10168.
Nakanotani et al., "Extremely Low-Threshold Amplified Spontaneous Emission of 9,9'-Spirobifluorene Derivatives and Electroluminescence From Field-Effect Transistor Structure", Advanced Functional Materials, 2007, vol. 17, p. 2328-2335.
Usluer et al., "Fluorene-Carbazole Dendrimers: Synthesis, Thermal, Photophysical and Electroluminescent Device Properties", Advanced Functional Materials, 2010, vol. 20, p. 4152-4161.

* cited by examiner

*Primary Examiner* — Gregory Clark
(74) *Attorney, Agent, or Firm* — Birch, Stewart, Kolasch & Birch, LLP

(57) ABSTRACT

In an embodiment, a carbazole derivative is provided. The carbazole derivative has formula (I):

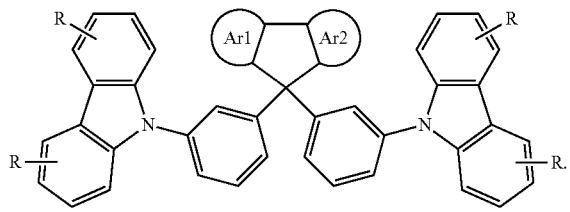

In formula (I), Ar1 and Ar2 are, independently, substituted or unsubstituted phenyl, naphthalenyl or heteroaryl containing nitrogen, oxygen or sulfur, and R is hydrogen, methyl or t-butyl. In another embodiment, an organic light emitting diode including the carbazole derivative is provided.

9 Claims, No Drawings

US 9,051,266 B2

CARBAZOLE DERIVATIVES AND ORGANIC LIGHT EMITTING DIODES COMPRISING THE SAME

CROSS REFERENCE TO RELATED APPLICATIONS

This application claims priority of Taiwan Patent Application No. 100139725, filed on Nov. 1, 2011, the entirety of which is incorporated by reference herein.

BACKGROUND

1. Field

The disclosure relates to a heterocyclic derivative, and more particularly to a carbazole derivative applied to organic light emitting diodes.

2. Description of the Related Art

An organic light emitting diode (OLED) has been deemed as a rising star of the flat panel display or lighting industry due to its excellent characteristics including light weight, thin profile, self-luminescence, low power consumption, no backlight requirement, no view angle limitation and high response rate etc. Considering the luminescence mechanism of phosphorescent materials in OLED devices, in order to achieve the best luminescence efficiency and quantum efficiency, the host materials with proper energy levels are required. Among them, blue phosphorescent host materials need a larger energy level gap, and such qualified molecules should have a shorter conjugated system, in addition, the thermal stability possessed by the host materials should also be considered. Therefore, the structural design for such host materials will be of corresponding difficulty. Most traditional commercially available host materials or those academically published for phosphorescent OLED devices are the derivatives containing carbazole fragments or multiple phenyl silicon functional groups. However, the known materials have problems of poor thermal stability or low current density resulting in over voltage. Therefore, development of host materials suitable for application to blue phosphorescent OLED devices is a very important topic.

BRIEF SUMMARY

One embodiment provides a carbazole derivative represented by formula (I):

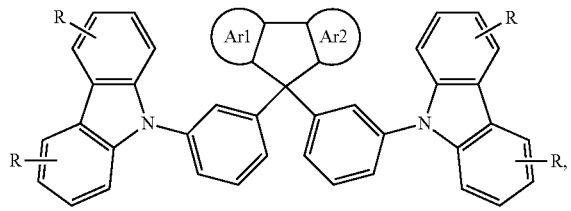

(I)

wherein Ar1 and Ar2 are, independently, substituted or unsubstituted phenyl, naphthalenyl or heteroaryl containing nitrogen, oxygen or sulfur, and R is hydrogen, methyl or t-butyl.

One embodiment provides an organic light emitting diode, comprising: a cathode and an anode; and a first light emitting layer disposed between the cathode and the anode, wherein the first emitting layer comprises the carbazole derivative represented by formula (I).

In the invention, the fluorene moiety possessing electron transport ability is exemplarily designed as the core structure. The carbazole moiety possessing hole transport ability is connected to the meta-position of the benzene ring connected to the carbon atom-9 of the fluorene moiety through a spiro connection. In this way, the conjugated system formed among the aromatic groups can be effectively blocked, improving the triplet energy level and thermal stability of the present carbazole derivative molecule. In the invention, the FIrpic is further utilized as a dopant for the blue phosphorescent host material. Also, the performance of devices can be effectively improved by combination of a conventional electron transport layer (ETL) and hole transport layer (HTL).

A detailed description is given in the following embodiments.

DETAILED DESCRIPTION

One embodiment provides a carbazole derivative represented by formula (I):

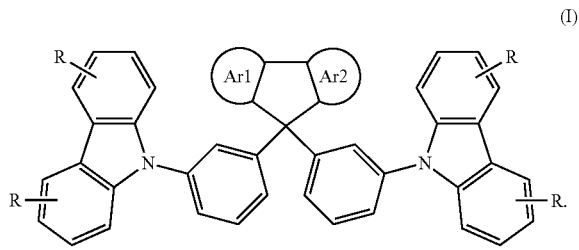

(I)

In formula (I), Ar1 and Ar2 may be, independently, substituted or unsubstituted phenyl, naphthalenyl or heteroaryl containing nitrogen, oxygen or sulfur. R may be hydrogen, methyl or t-butyl. In an embodiment, Ar1 and Ar2 may be, independently, C1-6 alkyl-substituted phenyl.

Some exemplary carbazole derivatives are shown as follows.

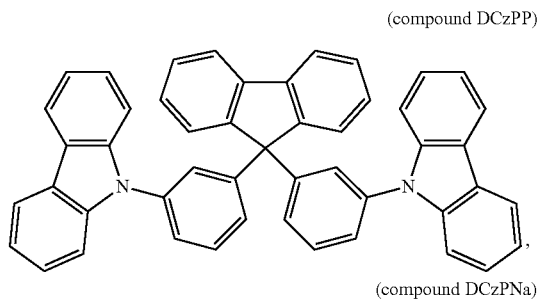

(compound DCzPP)

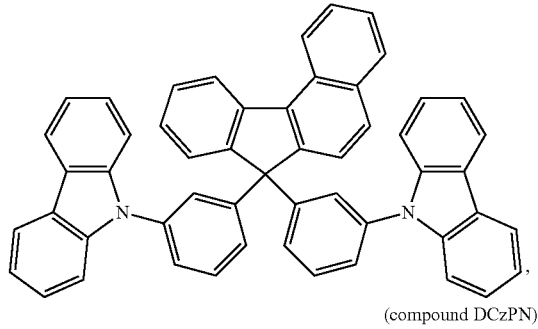

(compound DCzPNa)

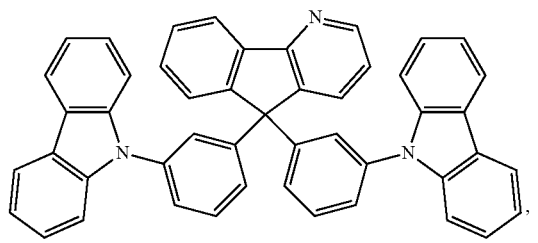

(compound DCzPN)

(compound DCzPO)
(compound DCzPS)
(compound DCzPC1)
(compound DCzPC2)
(compound DCzPC3)
(compound DCzPC4)
(compound DCzPC5)
(compound DCzPC6)

or

The disclosed carbazole derivative may be applied to organic light emitting diodes or organic solar cells.

One embodiment provides an organic light emitting diode comprising a cathode and an anode, and a first light emitting layer disposed between the cathode and the anode. The first light emitting layer comprises the carbazole derivative represented by formula (I).

The first light emitting layer may further comprise a dopant, for example iridium(III) bis(4,6-(difluorophenyl)-pyridinato-N,C') picolinate (FIrpic), with concentration of about 5-15%.

In an embodiment, the disclosed organic light emitting diode may further comprise a second light emitting layer disposed between the first light emitting layer and the anode. The second light emitting layer may comprise 4,4',4"-tris (carbazol-9-yl)triphenylamine (TCTA).

In an embodiment, the disclosed organic light emitting diode may further comprise a hole transport layer (HTL) disposed between the light emitting layer and the anode. The hole transport layer (HTL) may comprise 1,1-bis[(di-4-tolylamino)phenyl]cyclohexane (TAPC).

In an embodiment, the disclosed organic light emitting diode may further comprise an electron transport layer (ETL) disposed between the light emitting layer and the cathode. The electron transport layer (ETL) may comprise 1,3,5-tri[(3-pyridyl)-phen-3-yl]benzene (TmPyPB).

In the invention, the fluorene moiety possessing electron transport ability is exemplarily designed as the core structure. The carbazole moiety possessing hole transport ability is connected to the meta-position of the benzene ring connected to the carbon atom-9 of the fluorene moiety through a spiro connection. In this way, the conjugated system formed among the aromatic groups can be effectively blocked, improving the triplet energy level and thermal stability of the present carbazole derivative molecule. In the invention, the FIrpic is further utilized as a dopant for the blue phosphorescent host material. Also, the performance of devices can be effectively improved by combination of a conventional electron transport layer (ETL) and hole transport layer (HTL).

Example 1

Synthesis of the Present Host Material I (Compound DCzPP)

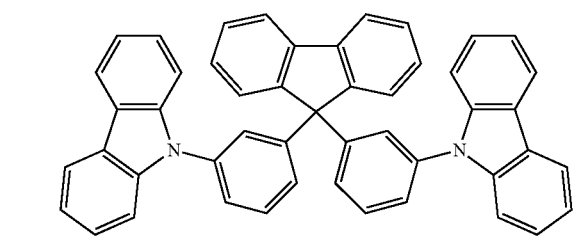 [SMILES: c1cc(-n2c3ccccc3c3ccccc32)cc(C2(c3cccc(-n4c5ccccc5c5ccccc54)c3)c3ccccc3-c3ccccc32)c1]

(1)

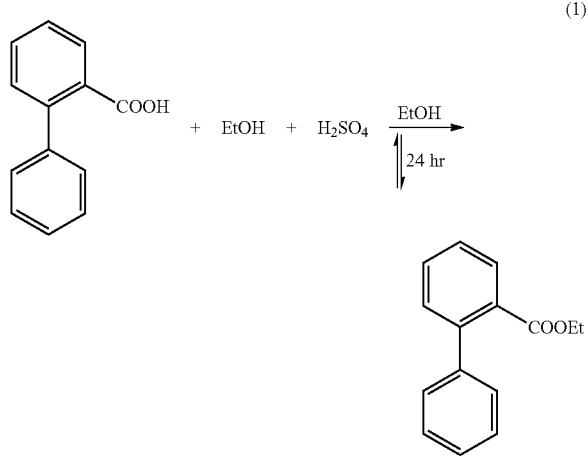

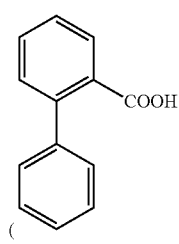

( )

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

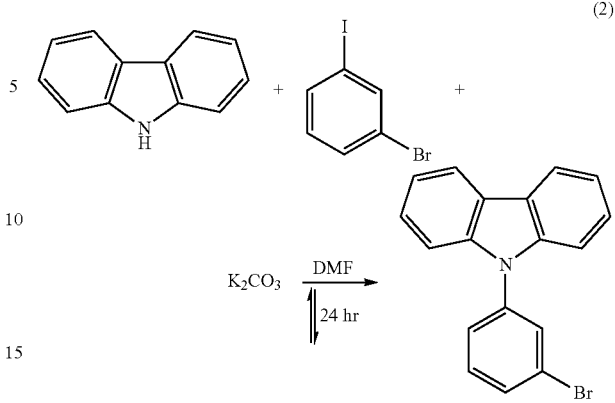

(2)

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel. Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

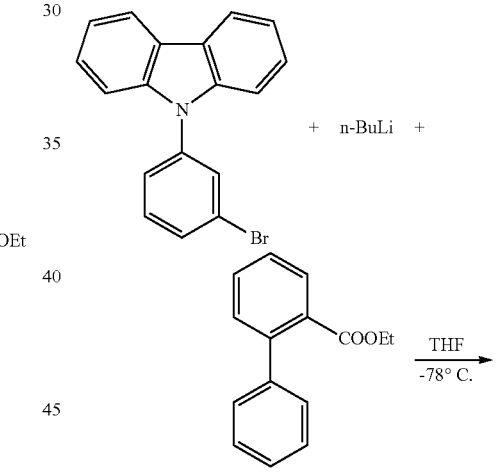

(3)

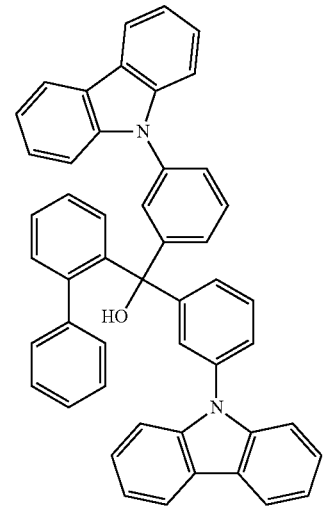

The starting material was dissolved in dried THF to form a solution and cooled to −78° C. Next, n-BuLi was slowly added to the solution. After 30 minutes, the dried ester starting material

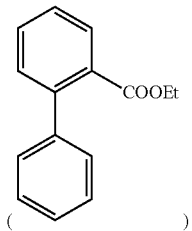

( )

was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

After the unpurified oily starting material

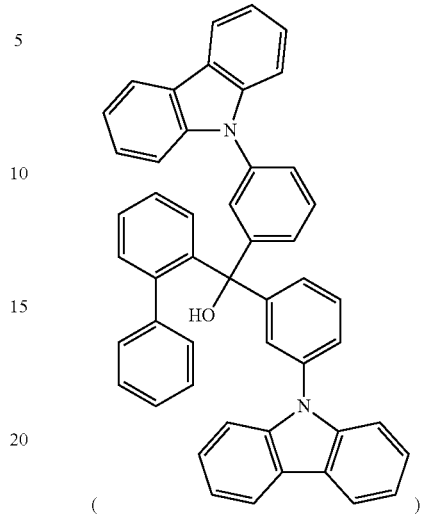

( )

was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPP was obtained.

Example 2

Synthesis of the Present Host Material II (Compound DCzPNa)

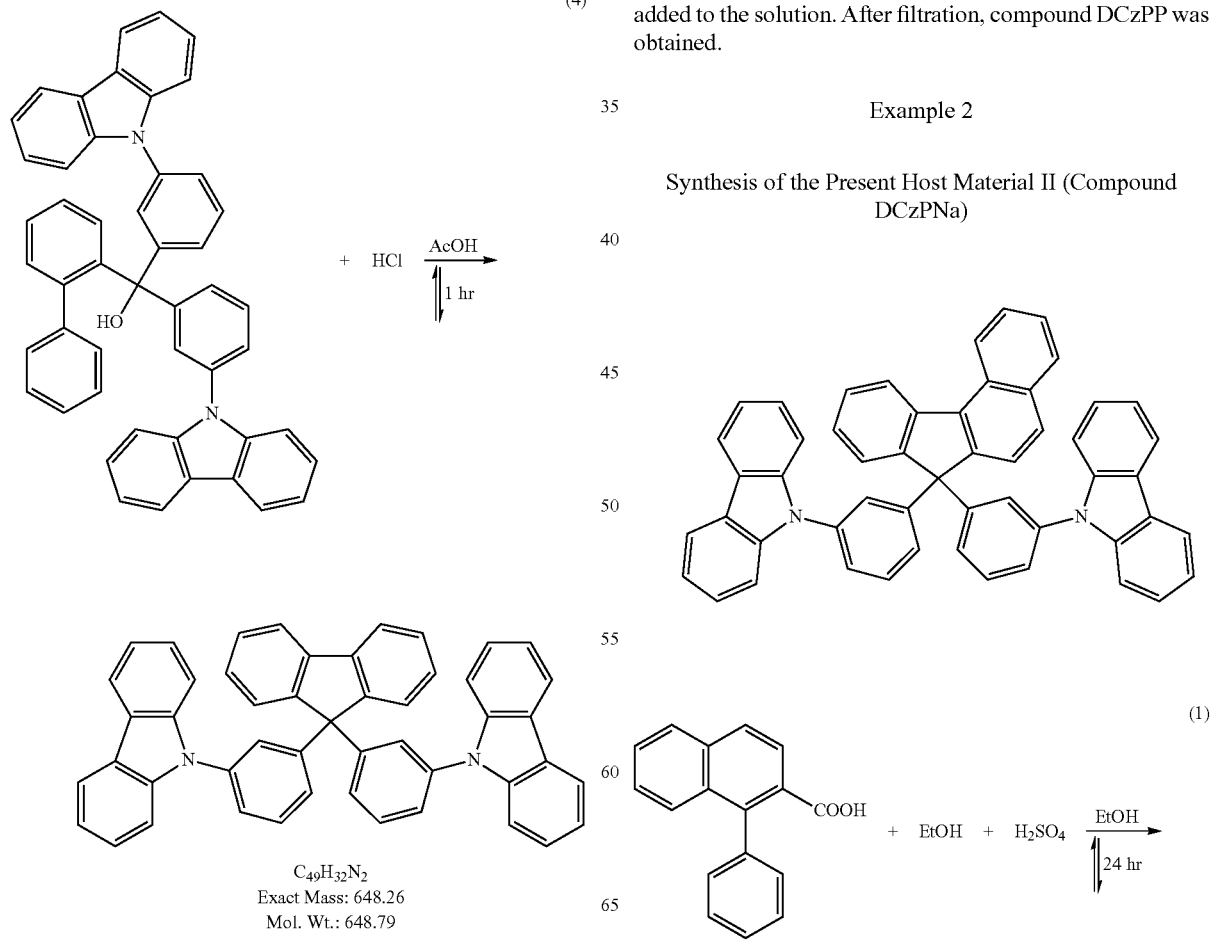

-continued

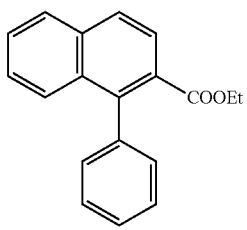

The starting material containing carboxyl group

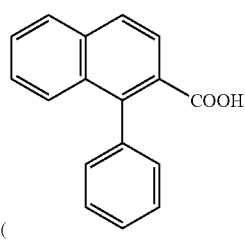

( )

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

(2)

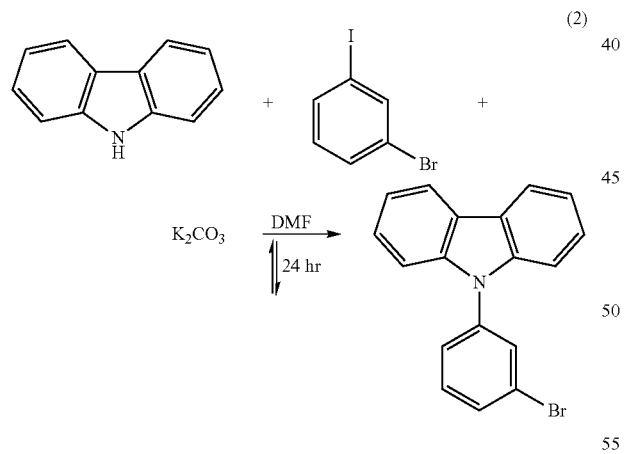

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel. Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

(3)

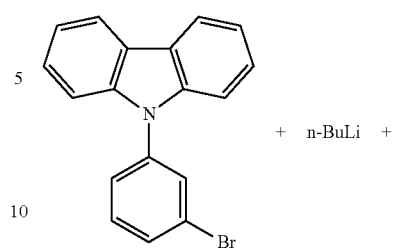

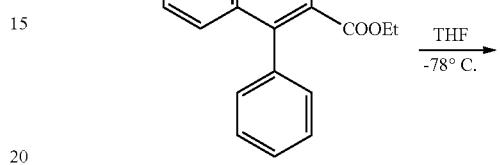

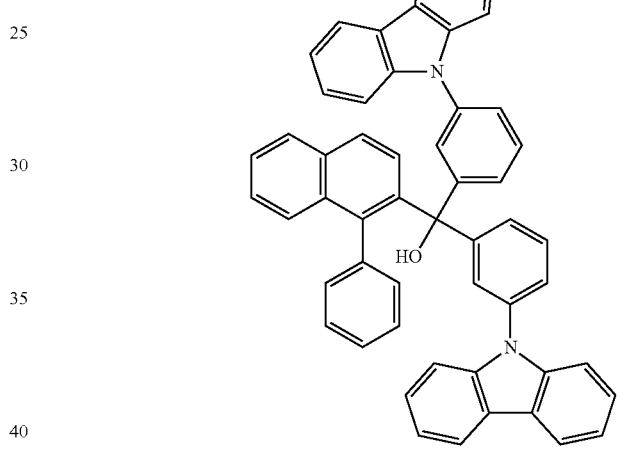

The starting material was dissolved in dried THF to form a solution and cooled to −78° C. Next, n-BuLi was slowly added to the solution. After 30 minutes, the dried ester starting material

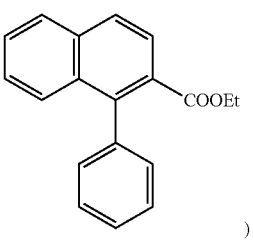

( )

was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

(4)

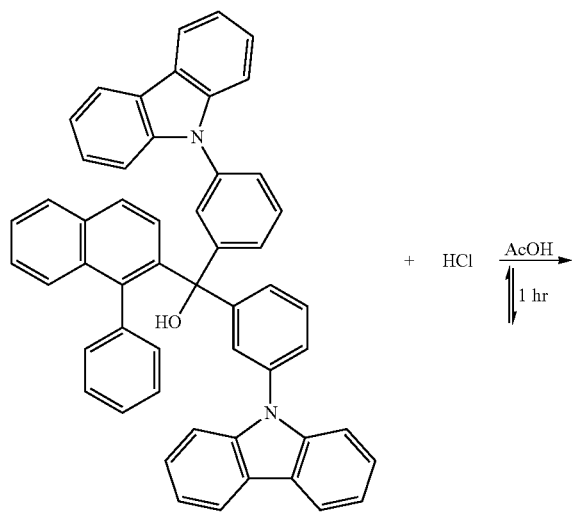

After the unpurified oily starting material

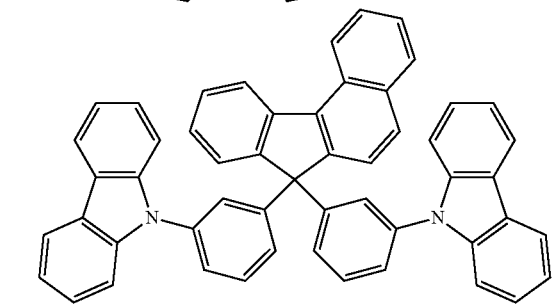

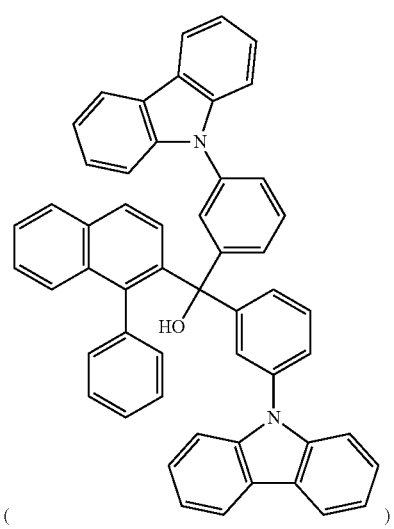

was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPNa was obtained.

Example 3

Synthesis of the Present Host Material III
(Compound DCzPN)

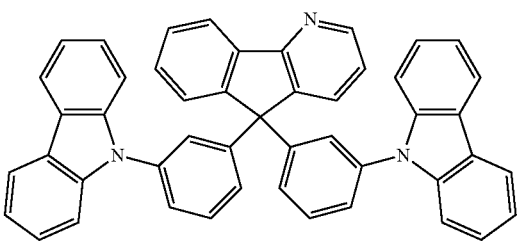 [SMILES: c1cc(-n2c3ccccc3c3ccccc32)cc(C2(c3cccc(-n4c5ccccc5c5ccccc54)c3)c3ccccc3-c3ncccc32)c1]

(1)

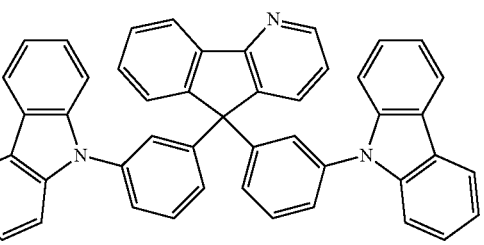

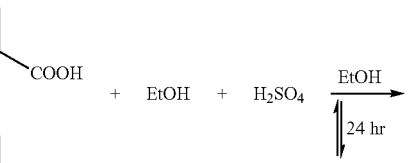

The starting material containing carboxyl group

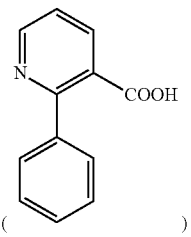

( )

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

(2)

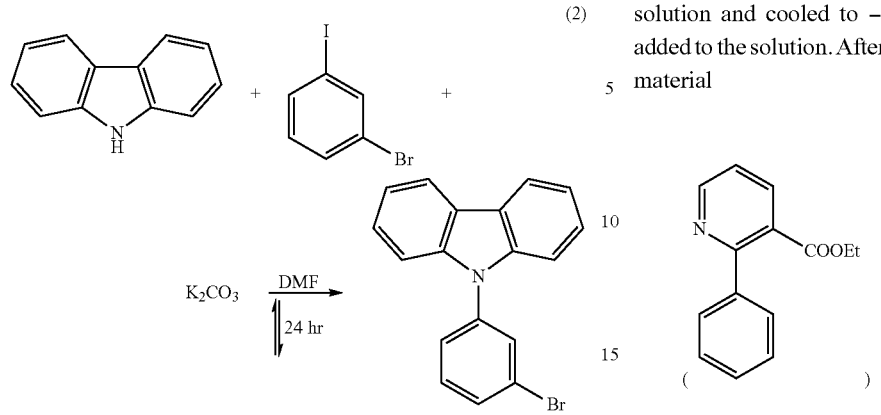

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel. Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

The starting material was dissolved in dried THF to form a solution and cooled to −78° C. Next, n-BuLi was slowly added to the solution. After 30 minutes, the dried ester starting material was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

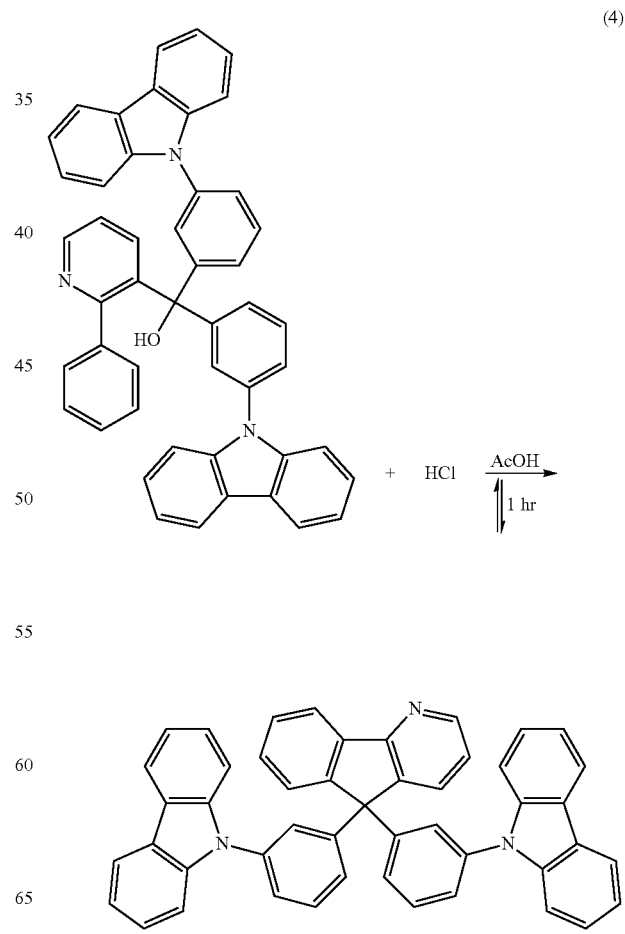

After the unpurified oily starting material

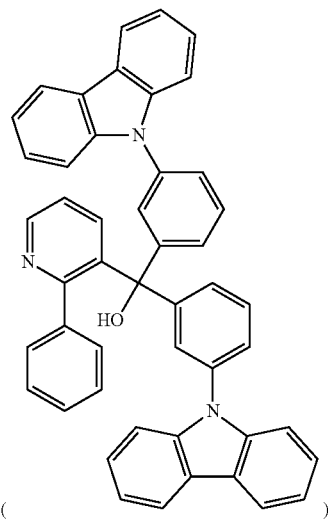

was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPN was obtained.

Example 4

Synthesis of the Present Host Material IV (Compound DCzPO)

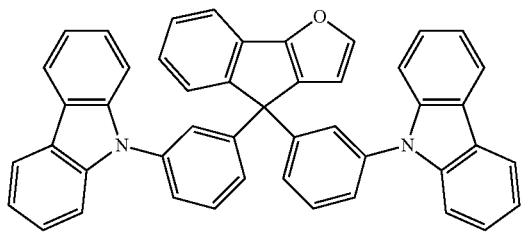 [SMILES: c1cc(-n2c3ccccc3c3ccccc32)cc(C2(c3cccc(-n4c5ccccc5c5ccccc54)c3)c3ccccc3-c3occc32)c1]

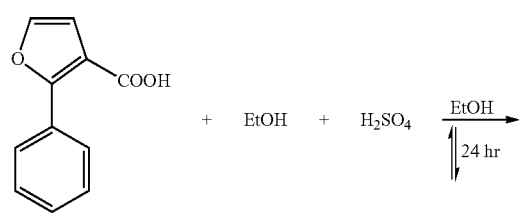

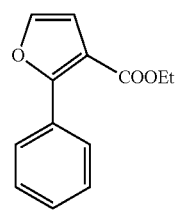

The starting material containing carboxyl group

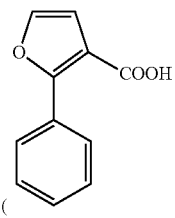

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

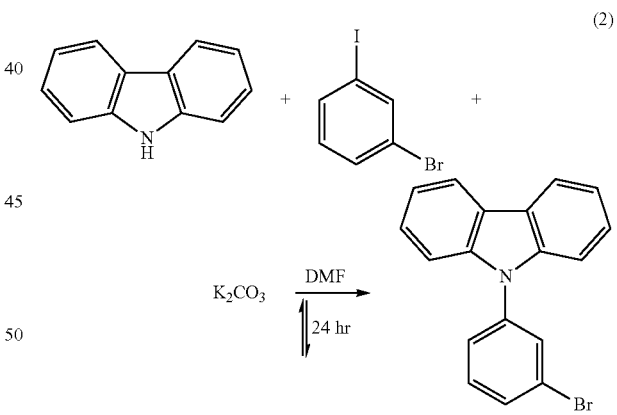

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

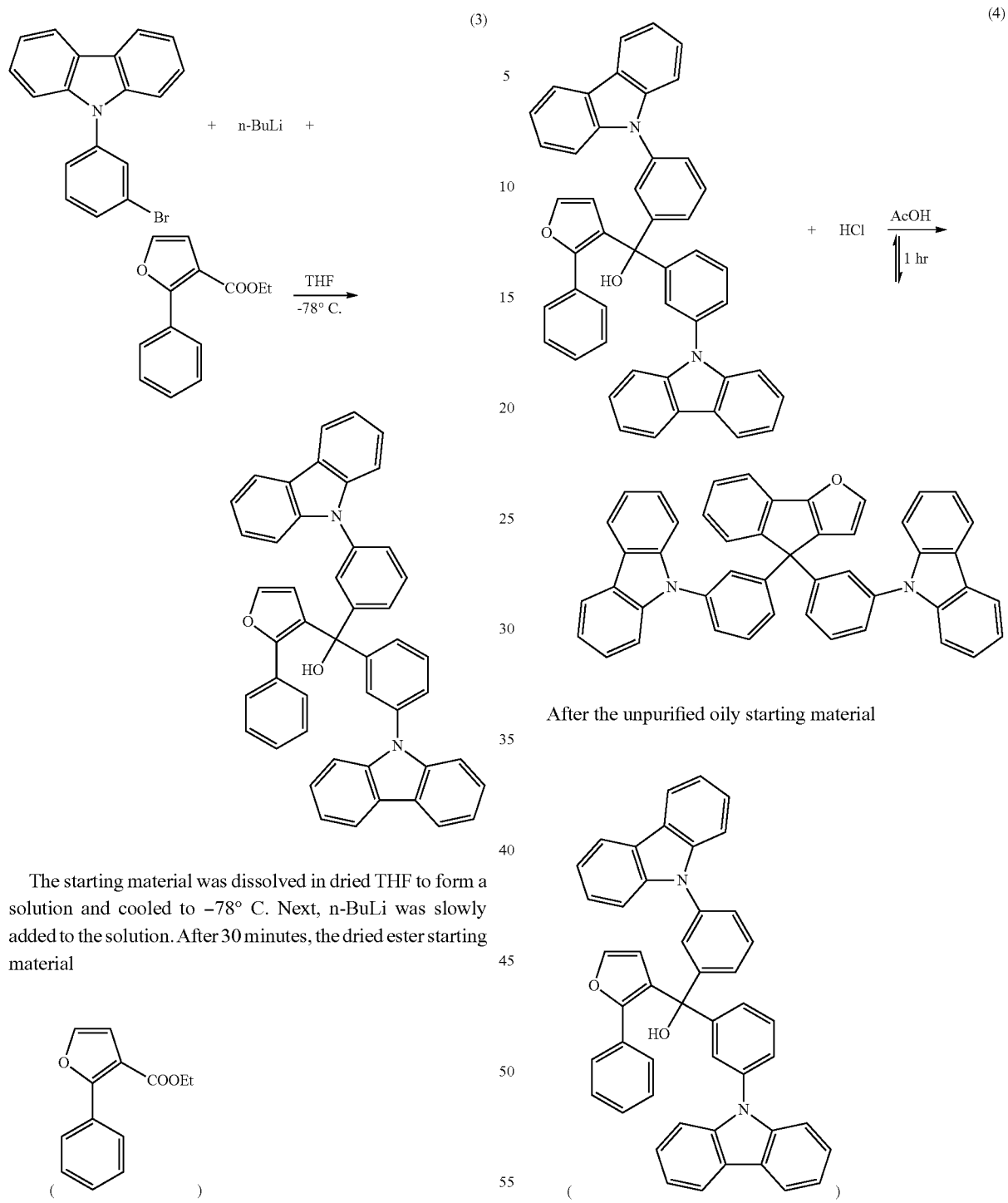

The starting material was dissolved in dried THF to form a solution and cooled to −78° C. Next, n-BuLi was slowly added to the solution. After 30 minutes, the dried ester starting material was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

After the unpurified oily starting material was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPO was obtained.

Example 5

Synthesis of the Present Host Material V (Compound DCzPS)

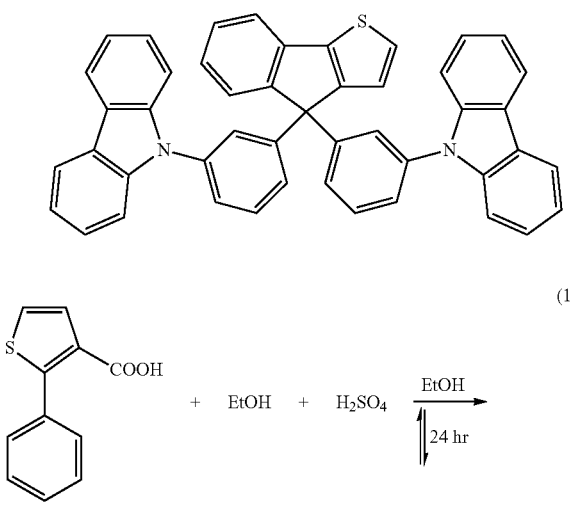

(1)

The starting material containing carboxyl group

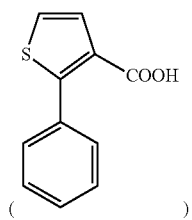

( )

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

(2)

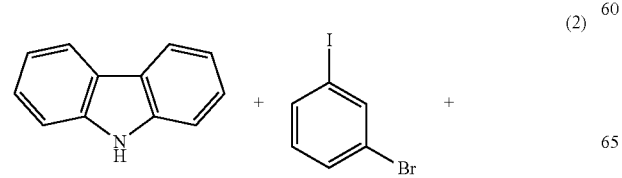

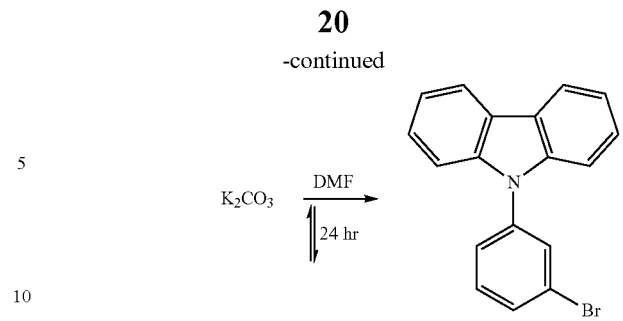

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel. Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

(3)

The starting material was dissolved in dried THF to form a solution and cooled to −78° C. Next, n-BuLi was slowly added to the solution. After 30 minutes, the dried ester starting material

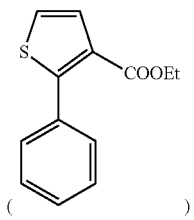

( )

was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

(4)

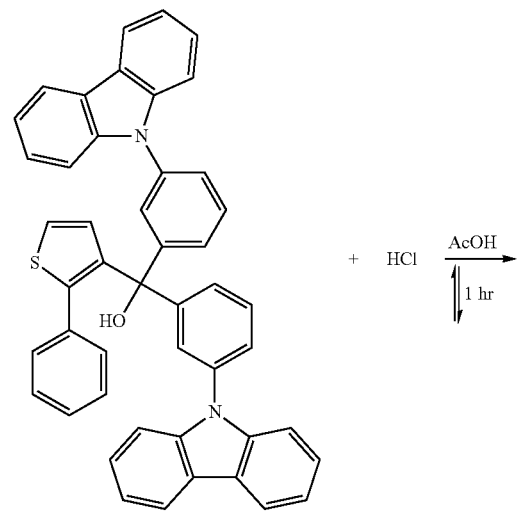

After the unpurified oily starting material

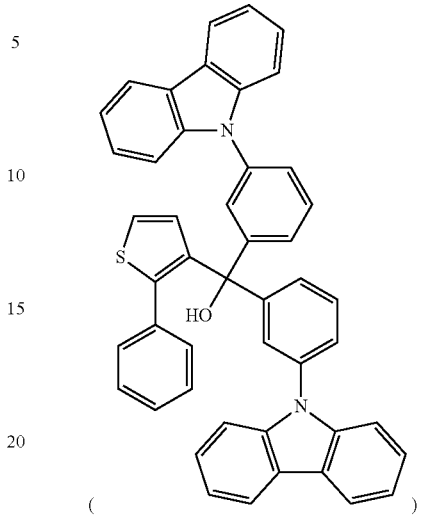

( )

was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPS was obtained.

Example 6

Synthesis of the Present Host Material VI
(Compound DCzPC1)

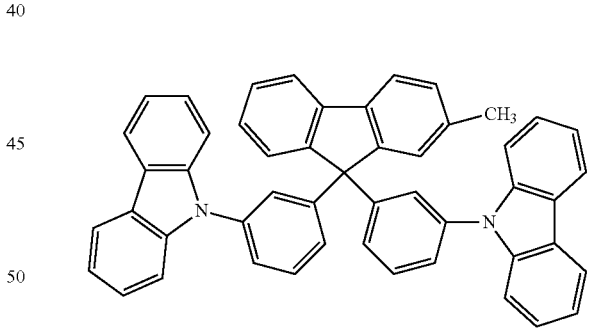

(1)

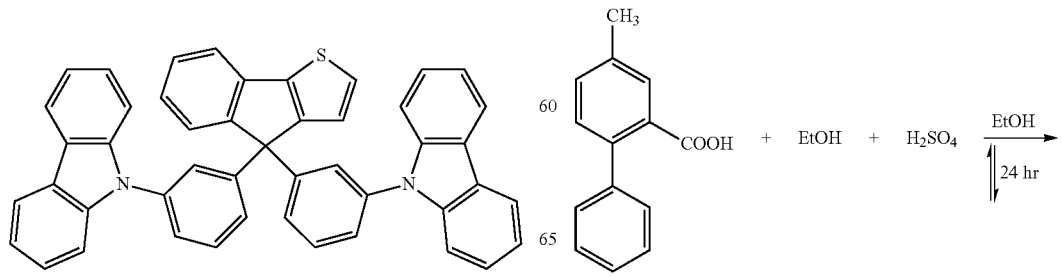

-continued

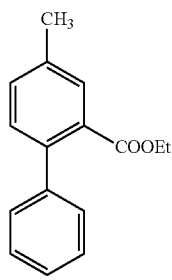

The starting material containing carboxyl group

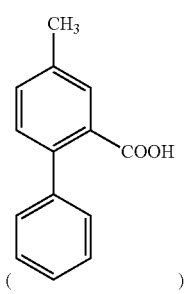
( )

and ethanol (EtOH) as a solvent and a reactant were blended to form a solution. About 2-4 drops of $H_2SO_4$ was then added to the solution and heated with reflux for about 24 hours. After cooling, an $NaHCO_3$ aqueous solution was slowly added to the solution to neutralize surplus acid until the solution achieved weak alkalinity. Most of the ethanol (EtOH) was then removed from the solution using a rotary concentrator. Next, the solution was extracted using ethyl acetate (EA) and water to collect the organic phase thereof. The organic phase was then dried.

(2)

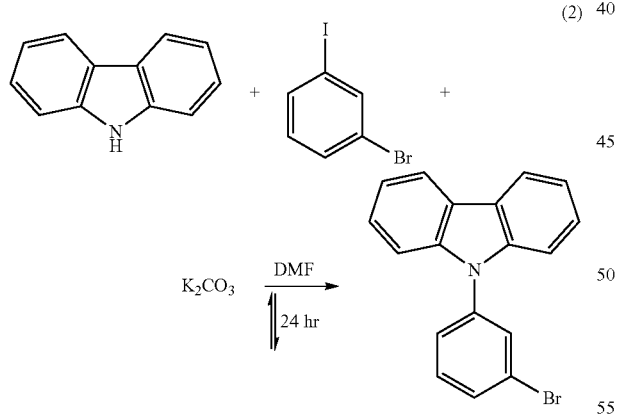

The two starting materials, alkali and DMF (without water removal) were blended in a 500 mL single-neck flask to form a solution and heated (about 150° C.) with reflux for 24 hours. After cooling, about 300 mL of ethyl acetate (EA) was added to the solution with stirring thoroughly. The solution was then filtered using a porcelain funnel. Salt and a solid were removed. Next, about 100 mL of a saline solution and 300 mL of water were added to the solution. The solution was then extracted using a proper amount of ethyl acetate (EA). After repeated extraction and exhausting, a rude product was obtained and purified using column chromatography.

(3)

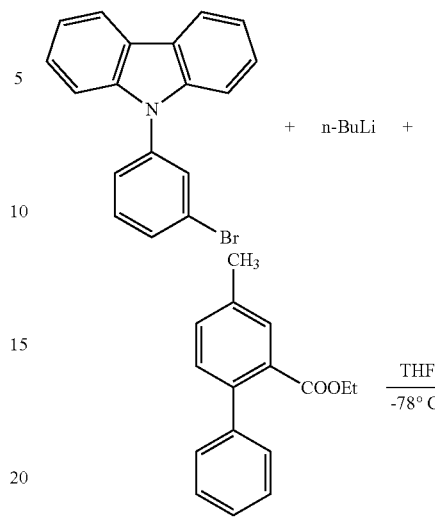

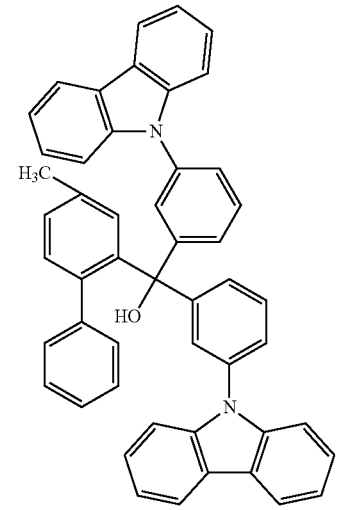

The starting material was dissolved in dried THF to form a solution and cooled to −78° C. Next, n-BuLi was slowly added to the solution. After 30 minutes, the dried ester starting material

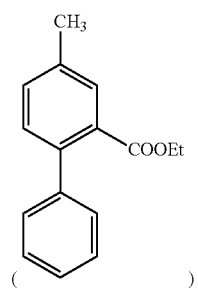
( )

was added to the solution and warmed to room temperature with stirring for about 10 minutes. The solution was then reacted with reflux under an oil bath for 2 hours. After warming to room temperature, the solution was extracted using ethyl acetate (EA) and water to collect the organic phase thereof. The organic phase was then exhausted to form an oily product. The next step was directly performed without purification.

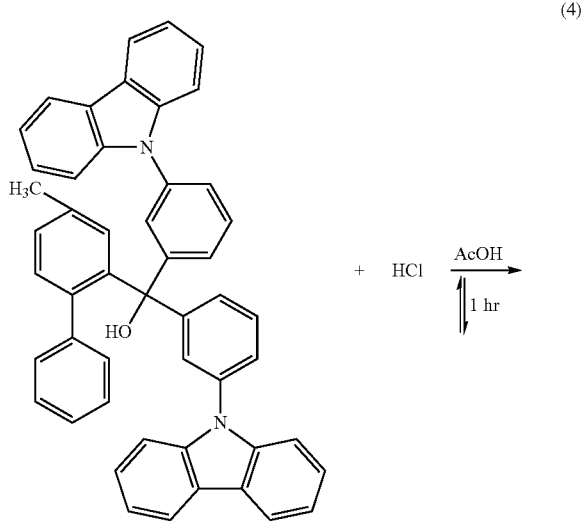

(4)

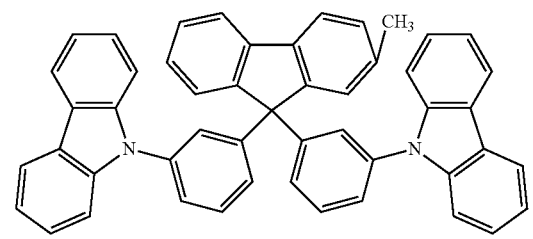

After the unpurified oily starting material

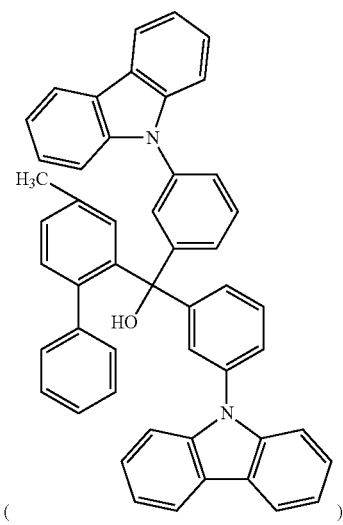

(  )

was exhausted, acetic acid was added thereto to form a solution. A few drops of HCl as an acid catalyst was then added to the solution. The solution was reacted with reflux for 1 hour under an oil bath. During reaction, white powder was gradually precipitated due to poor solubility of the product to solvent. When the reaction was completed, plenty of water was added to the solution. After filtration, compound DCzPC1 was obtained.

Example 7

The Physical Properties of the Present Host Materials (1) HOMO and LUMO Energy Levels HOMO and LUMO energy levels were calculated using AC3 and UV measuring instruments. First, a curve was measured using an AC3 instrument. A HOMO energy level was the intersection of two tangents. Energy level gap ($S_1$) was calculated from the UV spectrum. A LUMO energy level was obtained by subtracting the energy level gap ($S_1$) from HOMO energy level.

(2) Triplet Energy Level ($T_1$)

The shortest wavelength (onset) was measured using a low-temperature phosphorescence measurement technique of a fluorescence spectrometer. $T_1$ was calculated from the following equation.

$$T_1 = 1{,}240/\text{the shortest wavelength}$$

The comparisons of the physical properties (for example energy level gap ($S_1$), triplet energy level ($T_1$), HOMO energy level, LUMO energy level and glass transition temperature (Tg)) between the present host materials and conventional host materials are shown in Table 1.

TABLE 1

| Host materials | $S_1$ (eV) | $T_1$ (eV) | HOMO | LUMO | Tg (° C.) |
| --- | --- | --- | --- | --- | --- |
| DCzPP | 3.55 | 3.01 | 6.10 | 2.55 | 145 |
| DCzPNa | 3.41 | 2.70 | 5.96 | 2.55 | 151 |
| DCzPN | 3.54 | 2.78 | 6.02 | 2.48 | 147 |
| DCzPO | 3.52 | 2.62 | 5.94 | 2.42 | 136 |
| DCzPS | 3.55 | 2.57 | 5.96 | 2.41 | 135 |
| DCzPC1 | 3.54 | 2.97 | 6.05 | 2.51 | 146 |
| TCTA | 3.40 | 2.90 | 5.83 | 2.43 | 151 |
| CBP | 3.50 | 2.60 | 6.30 | 2.80 | 62 |
| mCP | 3.50 | 2.90 | 5.90 | 2.40 | 60 |

In accordance with Table 1, it is shown that the glass transition temperature (Tg) of the present host material DCzPP was greater than 140° C. The thermal stability of DCzPP was similar to that of the conventional blue phosphorescent host material TCTA. HOMO and LUMO energy levels of DCzPP were proper. When DCzPP was combined with a conventional electron transport layer (ETL) with a LUMO of 2.70 eV, the energy level gap therebetween was merely 0.15 eV, facilitating electron injection. Specifically, the energy level gap ($S_1$) of spiro-DCzPP improved to 3.55 eV. Also, the triplet energy level ($T_1$) thereof was improved to 3.01 eV, which is sufficient for use as an excellent blue phosphorescent host material for OLED devices.

Example 8

Fabrication and Performance Test of the Present Organic Light Emitting Diode I

First, an ITO glass substrate was provided to serve as an anode and washed with a cleaning agent and deionized water. After drying, TAPC was evaporated on the ITO glass substrate to form a hole transport layer (HTL). DCzPP and FIrpic (5-15%) were then co-evaporated on the hole transport layer to form a light emitting layer. Next, TmPyPB was evaporated on the light emitting layer to form an electron transport layer (ETL). $Cs_2CO_3$ was then evaporated on the electron transport layer to form a buffer layer. Finally, Al was evaporated on the buffer layer to form a cathode, to complete the description of the fabrication of an organic light emitting diode.

The element composition of the organic light emitting diode was as follows:

ITO/TAPC/DCzPP: FIrpic/TmPyPB/$Cs_2CO_3$/Al

The current efficiency and luminescence efficiency of the organic light emitting diodes fabricated by the present host material DCzPP combined with the dopant FIrpic with various concentrations under low current density (20 mA/$cm^2$) and high current density (1,000 cd/$m^2$) are shown in Table 2.

TABLE 2

| FIrpic concentration | Current efficiency (cd/A) | | Luminescence efficiency (lm/W) | |
|---|---|---|---|---|
| | 20 mA/$cm^2$ | 1,000 cd/$m^2$ | 20 mA/$cm^2$ | 1,000 cd/$m^2$ |
| 5% | 20.6 | 23.7 | 12.0 | 16.2 |
| 8% | 21.1 | 25.7 | 12.3 | 17.6 |
| 10% | 23.2 | 26.8 | 13.0 | 18.3 |
| 12% | 20.5 | 23.1 | 11.9 | 15.8 |
| 15% | 17.4 | 20.7 | 10.9 | 15.5 |

In accordance with Table 2, in this example, the organic light emitting diodes doped with the dopant FIrpic with various concentrations provide high current efficiency. Particularly, the current efficiency of the organic light emitting diode with 10% of the dopant FIrpic achieved 26.8 cd/A (1,000 cd/$m^2$).

Comparative Example 1

Fabrication and Performance Test of Conventional Organic Light Emitting Diodes

First, an ITO glass substrate was provided to serve as an anode and washed with a cleaning agent and deionized water. After drying, TAPC was evaporated on the ITO glass substrate to form a hole transport layer (HTL). TCTA and FIrpic (5-15%) were then co-evaporated on the hole transport layer to form a light emitting layer. Next, TmPyPB was evaporated on the light emitting layer to form an electron transport layer (ETL). And $Cs_2CO_3$ was then evaporated on the electron transport layer to form a buffer layer. Finally, Al was evaporated on the buffer layer to form a cathode, to complete the description of the fabrication of an organic light emitting diode.

The element composition of the organic light emitting diode was as follows:

ITO/TAPC/TCTA: FIrpic/TmPyPB/$Cs_2CO_3$/Al

The current efficiency and luminescence efficiency of the organic light emitting diodes fabricated by conventional host material TCTA combined with the dopant FIrpic with various concentrations under low current density (20 mA/$cm^2$) and high current density (1,000 cd/$m^2$) are shown in Table 3.

TABLE 3

| FIrpic concentration | Current efficiency (cd/A) | | Luminescence efficiency (lm/W) | |
|---|---|---|---|---|
| | 20 mA/$cm^2$ | 1,000 cd/$m^2$ | 20 mA/$cm^2$ | 1,000 cd/$m^2$ |
| 5% | 15.4 | 16.9 | 8.5 | 11.7 |
| 8% | 16.6 | 18.2 | 9.2 | 12.4 |
| 10% | 18.1 | 19.9 | 10.1 | 14.2 |
| 12% | 16.3 | 17.4 | 8.8 | 11.9 |
| 15% | 14.3 | 15.4 | 7.4 | 11.1 |

Similar to Example 8, the organic light emitting diode fabricated by the host material TCTA combined with 10% of the dopant FIrpic provided the highest current efficiency. However, the current efficiency of such organic light emitting diode was much lower than that of the organic light emitting diode fabricated by the present host material DCzPP.

Example 9

Fabrication and Performance Test of the Present Organic Light Emitting Diode II

First, an ITO glass substrate was provided to serve as an anode and washed with a cleaning agent and deionized water. After drying, TAPC was evaporated on the ITO glass substrate to form a hole transport layer (HTL). TCTA and FIrpic (10-15%) were then co-evaporated on the hole transport layer to form a first light emitting layer. DCzPP and FIrpic (10-15%) were then co-evaporated on the first light emitting layer to form a second light emitting layer. Next, TmPyPB was evaporated on the second light emitting layer to form an electron transport layer (ETL). $Cs_2CO_3$ was then evaporated on the electron transport layer to form a buffer layer. Finally, Al was evaporated on the buffer layer to form a cathode, to complete the description of the fabrication of an organic light emitting diode.

The element composition of the organic light emitting diode was as follows:

ITO/TAPC/TCTA:FIrpic/DCzPP:FIrpic/TmPyPB/$Cs_2CO_3$/Al

The current efficiency and luminescence efficiency of the organic light emitting diodes co-fabricated by the present host material DCzPP combined with the dopant FIrpic with various concentrations and conventional host material TCTA combined with the dopant FIrpic with various concentrations under low current density (20 mA/$cm^2$) and high current density (1,000 cd/$m^2$) are shown in Table 4.

TABLE 4

| FIrpic concentration | Current efficiency (cd/A) | | Luminescence efficiency (lm/W) | |
|---|---|---|---|---|
| | 20 mA/$cm^2$ | 1,000 cd/$m^2$ | 20 mA/$cm^2$ | 1,000 cd/$m^2$ |
| 10% | 27.2 | 33.3 | 18.6 | 27.5 |
| 15% | 25.8 | 30.2 | 17.6 | 23.7 |

In accordance with Table 4, under the illumination of 1,000 cd/$m^2$ and with 10% of the dopant, the luminescence efficiency of the present organic light emitting diode with dual light emitting layers achieved 27.5 lm/W, which is superior to that of the present organic light emitting diode with single light emitting layer.

While the disclosure has been described by way of example and in terms of preferred embodiment, it is to be understood that the disclosure is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A carbazole derivative represented by formula (I):

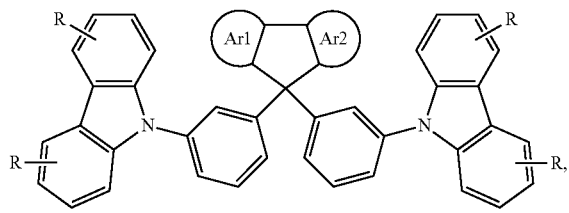

wherein

Ar1 and Ar2 are, independently, substituted or unsubstituted phenyl, naphthalenyl or heteroaryl containing nitrogen, oxygen or sulfur; and R is hydrogen, methyl or t-butyl.

2. The carbazole derivative as claimed in claim 1, wherein Ar1 and Ar2 are, independently, C1-6 alkyl-substituted phenyl.

3. The carbazole derivative as claimed in claim 1, wherein the carbazole derivative comprises

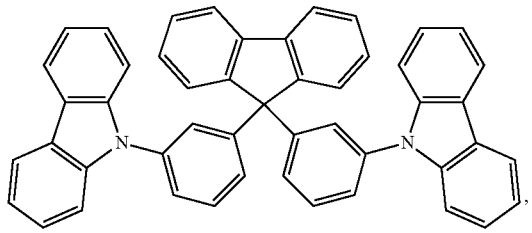

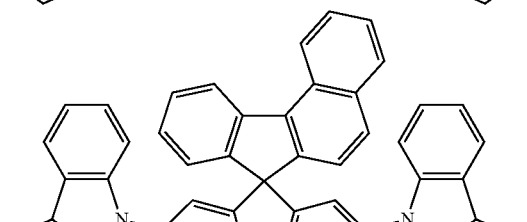

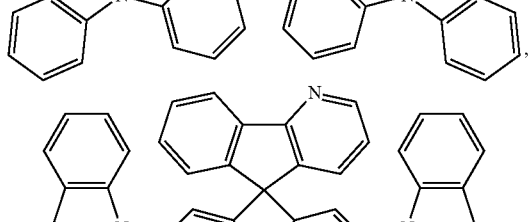

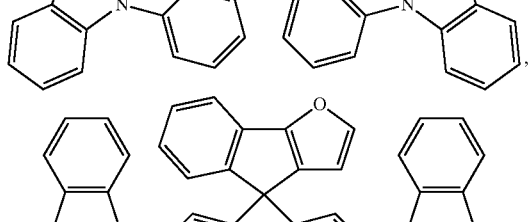

-continued

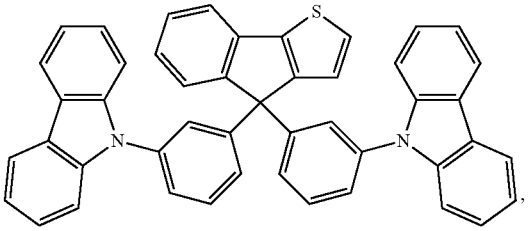

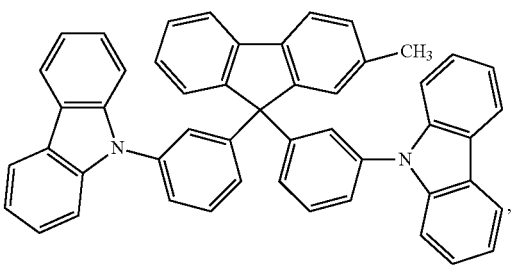

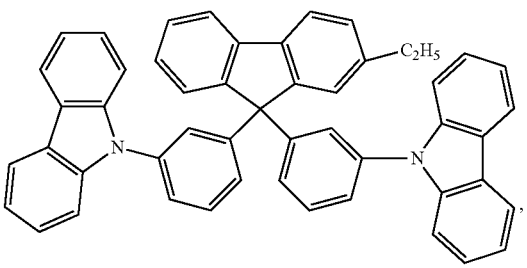

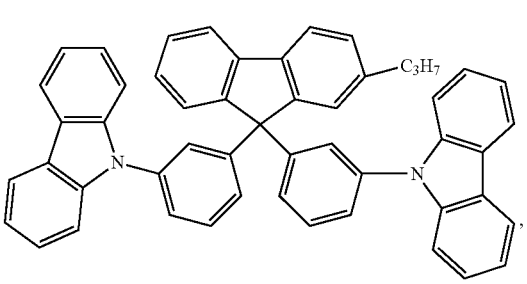

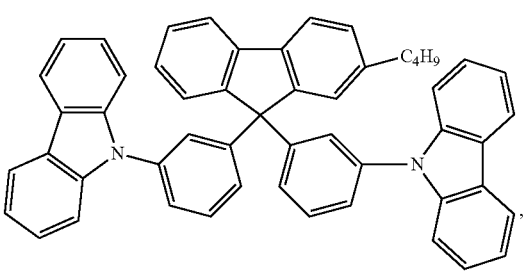

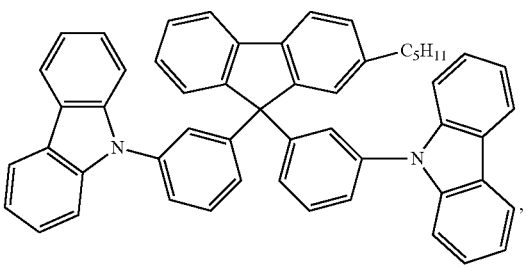

-continued

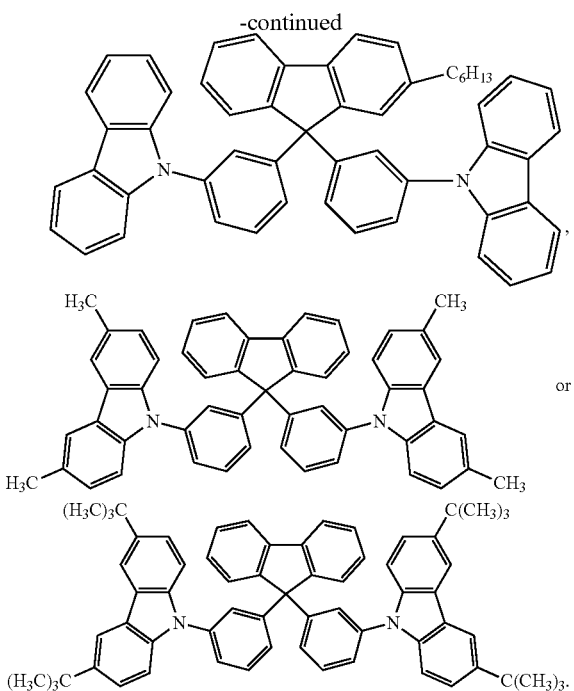

4. The carbazole derivative as claimed in claim 1, wherein the carbazole derivative is applied to organic light emitting diodes or organic solar cells.

5. An organic light emitting diode, comprising:
   a cathode and an anode; and
   a first light emitting layer disposed between the cathode and the anode, wherein the first light emitting layer comprises the carbazole derivative as claimed in claim 1.

6. The organic light emitting diode as claimed in claim 5, wherein the first light emitting layer further comprises a dopant.

7. The organic light emitting diode as claimed in claim 6, wherein the dopant has concentration of 5-15%.

8. The organic light emitting diode as claimed in claim 5, further comprising a second light emitting layer disposed between the first light emitting layer and the anode.

9. The organic light emitting diode as claimed in claim 8, wherein the second light emitting layer comprises 4,4',4"-tris (carbazol-9-yl)triphenylamine (TCTA).

* * * * *